(12) United States Patent
Kangas et al.

(10) Patent No.: US 7,136,759 B2
(45) Date of Patent: Nov. 14, 2006

(54) METHOD FOR ENHANCED ACCURACY IN PREDICTING PEPTIDES USING LIQUID SEPARATIONS OR CHROMATOGRAPHY

(75) Inventors: Lars J. Kangas, West Richland, WA (US); Kenneth J. Auberry, Kennewick, WA (US); Gordon A. Anderson, Benton City, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 395 days.

(21) Appl. No.: 10/323,387

(22) Filed: Dec. 18, 2002

(65) Prior Publication Data

US 2004/0121487 A1  Jun. 24, 2004

(51) Int. Cl.
*G06F 17/11* (2006.01)
*G06F 17/50* (2006.01)
*G06F 19/00* (2006.01)

(52) U.S. Cl. .......................... 702/19; 702/23; 530/417
(58) Field of Classification Search .................. 702/19, 702/27
See application file for complete search history.

(56) References Cited

OTHER PUBLICATIONS

Xie, Y L, et al "Modeling and Prediction of Retention in High Performance Liquid Chromatography by Using Neural Networks, CHROMATOGRAPHY." 1995 Germany vol. 41, No. 7-8-1995, pp. 935-444.

Goo, D et al "Prediction of Peptide Retention on Reversed Phase High Performance Liquid Chromatography. Determination of Retention Co-efficiency of Amino Acid Residues of Model Synthetic Peptides." Journal of Chromatography vol. 359, 1986, pp. 499-517.

Casel, V. et al "Comparative Prediction of the Retention Behavior of Small Peptides in Several Reverse Phase High Performance Liquid Chromatography Columns by Using Partial Least Squares and Multiple Linear Regression." Analytical Chemical ACTA, vol. 326, No. 23, pp. 77-84, 1996.

Cserhati, T. et al "Use of Multivariate Mathematical Methods for the Evaluation of Retention Data Matrices." Advances in Chromatography United States, 1996, vol. 36, pp. 1-63.

Botner, et al "Anomalous Reserved Phase High Performance Liquid Chromatographic Behavior of Synthetic Peptides Related to Antigenic Helper T Cell Sites." Journal of Chromatography, vol. 625, 1992, pp. 191-198.

(Continued)

*Primary Examiner*—Michael Borin
(74) *Attorney, Agent, or Firm*—Douglas E. McKinley, Jr.

(57) ABSTRACT

A method for predicting the elution time of a peptide in chromatographic and electrophoretic separations by first providing a data set of known elution times of known peptides, then creating a plurality of vectors, each vector having a plurality of dimensions, and each dimension representing the elution time of amino acids present in each of these known peptides from the data set. The elution time of any protein is then be predicted by first creating a vector by assigning dimensional values for the elution time of amino acids of at least one hypothetical peptide and then calculating a predicted elution time for the vector by performing a multivariate regression of the dimensional values of the hypothetical peptide using the dimensional values of the known peptides. Preferably, the multivariate regression is accomplished by the use of an artificial neural network and the elution times are first normalized using a transfer function.

9 Claims, 6 Drawing Sheets

OTHER PUBLICATIONS

Yan, et al "Large Artificial Neural Networks Applied to the Prediction of Retention Indices of Acyclic and Cyclic Alkanes, Alkenes, Alcohols. Esters, Katones and Ethers." Computer Chem., vol. 72, 5, pp. 405-412, 1998.

Sanz, Nebot, et al "Prediction of Retention Behavior and Evaluation of pKa Values of Peptides and quinolones in Liquid Chromatography" Journal of chromatography, vol. 933, pp. 45-56, 2001.

Wilce, et al "High Performance Liquid Chromatography of Amino Acids, Peptides and Proteins." Journal of Chromatography, vol. 536, pp. 165-183, 1991.

Skecnik, et al "Optimization of Artificial Neural Network Used for Retention Modeling in Ion Chromatography." Journal of Chromatography, vol. 973, pp. 47-59, 2002.

Jalili-Heraui, et al "Use of Self-Training Artificial Neural Network in Modeling of Gas Chromatographic Relative Retention Times in a Variety of Organic Compounds." Journal of Chromatography, vol. 945, pp. 173-184, 2002.

Sacchero, et al "Comparison of prediction power between theoretical and neural network models in ion-interaction chromatography" Journal of Chromatography vol. 799 1998 pp. 35-45.

Zhao et al. "Application of an artificial neural network in chromatography-retention behavior prediction and pattern recognition" Chromatography and Intellegent Laboratory Systems vol. 45 1999 163-170.

Meek et al "Factions affecting retention and resolution of peptides in high performance liquid chromatography" Journal of Chromatography vol. 211 1981 p. 171-179.

Van et al Use of artificial neural networks to predict the gas chromatograph retention index data of alkylbenzenes on carbowavium Computers and Chemistry vol. 24 2000 p. 171-179.

Yoshida et al, "Prediction of peptide retention times in normal phase liquid chromatography with only a single gradient run" Journal of Chromatography A vol. 841 1999 pp. 19-32.

Madden et al, "Prediction of peptide retention times for anions in linear gradient elution ion chromatography with hydroxide eluents using artificial neural networks" Journal of Chromatography A vol. 916 2001 pp. 173-179.

Eisenberg et al "The hydrophobic moment detects periodicity in protein hydrophobicity" Biophysics vol. 81 1884 pp. 140-144.

Palmblad et al "Prediction of Chromatographic Retention and Protein Identification in Liquid Chromatography/Mass Spectrometry" Anal Chemistry 2002 vol. 79 pp. 5826-5830.

Wilce et al "High Performance Liquid Chromatography of Amino Acids, Peptides and Proteins" Journal of Chromatography vol. 632 1993 pp. 11-18.

Lochmuller et al "Current Strategies for Prediction of Retention in High Performance Liquid Chromatography" Journal of Chromatography vol. 656 1993 pp. 3-18.

Peterson, et al "Counter-Propagation Neural Networks in the Modeling and Prediction of Kovats Indices for Substituted Rheols." Anal. Chem.1992. vol. 64, p. 379-386.

Ko, et al "Comparison of Selected Retention Models in Reversed Phase Liquid Chromatography." Journal of Chromatography, vol. 913, 2001, pp. 3-13.

Loukas, "Artificial Neural Networks in Liquid Chromatography: Efficient and Improved Quantitative Structure-Retention Relationship Models." Journal of Chromatography, vol. 904, 2000, pp. 119-129. Purcel, et al "High Performance Liquid Chromatography of Amino Acids, Peptides and Proteins." Journal of Chromatography, vol. 476, 1989, pp. 113-123.

Song, et al "Prediction of Protein Retention Times in Anion-Exchange Chromatography Systems Using Support Vector Regression." Journal of Chromatography Inf. Sci., vol. 42, 2002 pp. 1347-1357.

Hallgren, "Prediction of Protein Retention at Gradient Elution Conditions in Ion-Exchange Chromatography." Journal of Chromatography A, vol. 852, 1999, pp. 351-359.

Li, et al "Evaluation of the Retention Dependence on the Physicochemical Properties of Solutes in Reversed-Phase Liquid Chromatographic Linear Gradient Elution Based on Linear Solvation Energy Relationships." Journal of Chromatography A, vol. 905, 2001, pp. 35-46.

Browne, et al "The Isolation of Peptides by High-Performance Liquid Chromatography Using Predicted Elution Positions." Analytical Biochemistry, vol. 124, 1982, pp. 201-208.

Houghten, et al "Effect of Positional Environmental Domains on the Variation of High Performance Liquid Chromatographic Peptide Retention Coefficients." Journal of Chromatography, vol. 386, 1987, pp. 223-228.

Sacchero, et al "Comparison of Prediction Power Between Theoretical and Neural-Network Models in Ion-Interaction Chromatography." Journal of Chromatography, vol. 799, 1998, pp. 35-45.

Lienqueo, et al, "Mathematical Correlation for Predicting Protein Retention Times in Hydrophobic Interaction Chromatography." Journal of Chromatography A, vol. 978, 2002, pp. 71-79.

Mant, et al "Effect of Peptide Chain Length on Peptide Retention Behavior in Reversed-Phase Chromatography." Journal of Chromatography, vol. 458, 1988, pp. 193-205.

Meek, "Prediction of Peptide Rete4ntion Times in High-Pressure Liquid Chromatography on the Basis of Amino Acid Composition." Proc. Natl. Acad. Sci. USA, vol. 77, No. 3, 1980, pp. 1632-1636.

Zhao, et al "Application of the Artificial Neural Network in a Study of the Relationship Between Retention Index and Molecular Structure Parameters in MECC." American Laboratory, Sep. 2000, pp. 13-14.

SEQUENCE LISTING

```
<160> NUMBER OF SEQ ID NOS: 9

<210> SEQ ID NO 1
<211> LENGTH: 16
<212> TYPE: PRT
<213> ORGANISM: Deinococcus radiodurans

<400> SEQUENCE: 1

Leu Pro Asn His Ile Gln Val Asp Asp Leu Arg Gln Leu Leu Asp Val
1               5                   10                  15

<210> SEQ ID NO 2
<211> LENGTH: 16
<212> TYPE: PRT
<213> ORGANISM: Deinococcus radiodurans

<400> SEQUENCE: 2

Val Ala Ile Asn Asp Thr Asp Asn His Thr Leu Ala His Leu Leu Lys
1               5                   10                  15

<210> SEQ ID NO 3
<211> LENGTH: 6
<212> TYPE: PRT
<213> ORGANISM: unknown
<220> FEATURE:
<223> OTHER INFORMATION: illustrative example

<400> SEQUENCE: 3

Ile Val Ile Glu Ile Lys
1               5

<210> SEQ ID NO 4
<211> LENGTH: 6
<212> TYPE: PRT
<213> ORGANISM: unknown
<220> FEATURE:
<223> OTHER INFORMATION: illustrative example

<400> SEQUENCE: 4

Val Ile Leu Leu Glu Lys
1               5

<210> SEQ ID NO 5
<211> LENGTH: 14
<212> TYPE: PRT
<213> ORGANISM: unknown
<220> FEATURE:
<223> OTHER INFORMATION: illustrative example

<400> SEQUENCE: 5

Gln Thr Phe Glu Ala Ala Ile Leu Thr Gln Leu His Pro Arg
1               5                   10

<210> SEQ ID NO 6
<211> LENGTH: 14
<212> TYPE: PRT
<213> ORGANISM: unknown
<220> FEATURE:
<223> OTHER INFORMATION: illustrative example

<400> SEQUENCE: 6

Thr Leu His Ser Leu Thr Gln Trp Asn Gly Leu Ile Asn Lys
1               5                   10
```

-continued

```
<210> SEQ ID NO 7
<211> LENGTH: 15
<212> TYPE: PRT
<213> ORGANISM: unknown
<220> FEATURE:
<223> OTHER INFORMATION: illustrative example

<400> SEQUENCE: 7

Leu Leu Phe Leu Val Gly Thr Ala Ser Asn Pro His Glu Ala Arg
1               5                   10                  15

<210> SEQ ID NO 8
<211> LENGTH: 11
<212> TYPE: PRT
<213> ORGANISM: unknown
<220> FEATURE:
<223> OTHER INFORMATION: illustrative example

<400> SEQUENCE: 8

Ala Asn Ala Ala Ile Asn Ser Gly Ala Phe Lys
1               5                   10

<210> SEQ ID NO 9
<211> LENGTH: 10
<212> TYPE: PRT
<213> ORGANISM: unknown
<220> FEATURE:
<223> OTHER INFORMATION: illustrative example

<400> SEQUENCE: 9

Ile Ile Ala Ala Gly Ala Asn Val Val Arg
1               5                   10
```

METHOD FOR ENHANCED ACCURACY IN PREDICTING PEPTIDES USING LIQUID SEPARATIONS OR CHROMATOGRAPHY

STATEMENT REGARDING FEDERALLY SPONSORED RESEARCH OR DEVELOPMENT

This invention was made with Government support under Contract DE-AC0676RLO1830 awarded by the U.S. Department of Energy. The Government has certain rights in the invention.

CROSS-REFERENCE TO RELATED APPLICATIONS

Not Applicable

REFERENCE TO SEQUENCE LISTING

Each protein sequence described herein has been submitted to the United States Patent and Trademark Office on a compact disc in computer readable form in compliance with 37 CFR §§ 1.821–1.825. A paper copy of that submission is attached herewith. The sequence listing information recorded in computer readable form is identical to the written sequence listing.

BACKGROUND OF THE INVENTION

Liquid phase separations (eg. liquid chromatography and electrophoretic separations) have long been used as investigative tools by scientists and researchers seeking to identify the structure of molecules, particularly peptides (as used herein the term "peptides" refers to polymers having more than one amino acid, and includes, without limitation, dipeptides, tripeptides, oligopeptides, and polypeptides. The term "protein" refers to molecules containing one or more polypeptide chains).

Proteomics involves the broad and systematic analysis of proteins, which includes their identification, quantification, and ultimately the attribution of one or more biological functions. Proteomic analyses are challenging due to the high complexity and dynamic range of protein abundances. The industrialisation of biology requires that the systematic analysis of expressed proteins be conducted in a high-throughput manner and with high sensitivity, further increasing the challenge. Recent technological advances in instrumentation, bio-informatics and automation have contributed to progress towards this goal. Specifically, in the area of proteomic identification, it is evident that greater specificity benefits the ability to deal with the high complexity of proteomes. As a result, recent efforts have focused on improvements in separation speed, resolving power and dynamic range, and these methods have generally been based on the combination of separations with mass spectrometry (MS), using correlation of tandem mass spectra with established protein databases or predictions from genome sequence data for identifications.

Additionally, modern proteomics research has increasingly taken advantage of the ability of liquid chromatography to identify proteins from their elution time from a chromatographic column. The information gleaned from a liquid chromatograph can be enhanced by identifying the molecule's mass, or mass to charge, by coupling the liquid chromatograph either on line or off line, with a mass spectrometer. Common methods include offline tryptic digestion and subsequent electrophoretic or chromatographic separation with matrix-assisted laser desorption/ionization or electrospray time-of-flight or ion trap mass spectrometry. Capillary electrophoresis, mass spectrometry or liquid chromatography/mass spectrometry coupled online via electrospray interfaces have also been used to analyze tryptic and other digests of complex biological samples such as whole cell lysates and human body fluids. The dynamic range of the mass spectrometer in these methods may be limited when a sample is directly infused by ion suppression in the electrospray and the detector. Further, the dynamic range of Fourier transform ion cyclotron resonance (FTICR) and ion trap mass spectrometers can be limited by the storage capacity within the instrument, although it has been shown that the use of a mass selective quadrupole to selectively load the FTICR cell.

Researchers attempting to enhance the accuracy of these methods have devised a number of schemes to increase their accuracy. For example, in the paper "Prediction of Chromatographic Retention and Protein Identification in Liquid Chromatography/Mass Spectrometry" Magnus Palmblad, Margareta Ramstrom, Karin E. Markides, Per Hakansson, and Jonas Bergquist, *Analytic Chemistry* p. 4–9, 2002, the authors describe a method for using the information from liquid separation schemes such as chromatography and electrophoretic methods, to improve peptide mass fingerprinting based on accurate mass measurement. The author's concede that the resolving power and accuracy in chromatographic separations are several orders of magnitude lower than in mass spectrometry, but they contend that the information is complementary in nature and available at negligible computational cost and at no additional experimental cost. Briefly, the method described in the Palmblad paper assigns "retention coefficients" for the 20 amino acids, as well as the number of each amino acid, a term that compensates for void volumes and a delay between sample injection and acquisition of mass spectra. The parameters are then fitted by the least squares method to experimental data from ~70 BSA peptides of ~100 HAS and transferrin peptides putatively identified by accurate mass measurement and high relative intensities in the mass spectra. The authors found that "the accuracy of the predictor was found to be 8–10% when "trained" by each of the six BSA and CSF data sets." While approaches such as that described in the Palmblad paper provide some useful information, their utility is limited by the accuracy of the predictions.

Thus, at the present, there are two major approaches for proteomic analyses. The first one consists of the off-line combination of two-dimensional polyacrylamide electrophoresis (2D-PAGE) with MS. The proteins are first separated in a gel by their pI and mass and then the protein "spots" are enzymatically hydrolysed resulting in peptide mixtures which are analysed by matrix assisted laser desorption ionisation-time of flight (MALDI-TOF) or electrospray (ESI)-MS. Another rapid evolving approach consists of a global proteome-wide enzymatic digestion followed by analysis using on-line 1-D or 2-D liquid chromatography (LC) coupled with ESI-MS. The detection of the peptides is achieved by tandem MS (7,13) or more recently by single stage Fourier transform ion cyclotron resonance (FTICR)-MS, which provides high sensitivity, large dynamic range and high throughput in routine applications by circumventing the need for tandem MS.

An aspect of proteomic analysis that has not yet been exploited involves use of the information available from the separations (eg. LC elution time). Indeed, retention time in LC is unique and structurally dependent for a defined experiment (mobile phase composition, stationary phase etc.). If there is a way to predict the LC retention time for a given peptide structure, then this could be used in conjunction with either MS/MS data to improve the confidence of peptide identifications and/or increase the number of peptide identifications, or, with sufficiently high accuracy MS, to reduce the need for MS/MS data (i.e. if the prediction is reliable enough).

The idea that chromatographic behaviour of peptides could be predicted based on the amino acid composition is not new. In 1951, Knight and Pardee showed that synthetic peptides retention factor ($R_f$) values on paper chromatography could be predicted with some accuracy. In 1952, Sanger introduced the problem of isomers by demonstrating that the relationship between $R_f$ and composition was not absolutely accurate since peptides containing the same amino acids but having difference sequences could frequently be separated. More recently, there have been several reports on the prediction of peptide elution times in reversed-phase (RP) or normal phase liquid chromatography. These methods used quantitative structure-chromatographic retention relationships (QSRR's) (e.g. partial least square or multiple linear regression) for the peptide elution time prediction. Casal et al. demonstrated that partial least squares regression provides a better predictive ability with these models using a mixture of 25 small standard peptides. One limitation of these models is that they are most effective for peptides with less than 15–20 amino acid residues.

Another approach, based on artificial neural networks (ANNs), has demonstrated better predictive capabilities in several areas of chemistry including: (i) conformational states for small peptides (31), (ii) carbon-13 nuclear magnetic resonance chemical shifts and (iii) the retardation factor or retention time of small molecules in thin layer chromatography, GC and LC. While these advances are significant, until the present invention, those having skill in the art have not yet used ANNs for peptide elution time prediction.

Accordingly, there remains a need for improved methods for predicting the identity of peptides and proteins.

BRIEF SUMMARY OF THE INVENTION

Accordingly, iris an object of the present invention to provide a method for predicting the elution or retention times of chemically related compounds such as proteins and peptide in liquid separations. As used herein, "liquid separations" includes, but is not limited to, liquid chromatography, both standard and reverse phase, electrophoretic separations, such as capillary electrophoresis; field flow fractionation, and methods whereby one or more of these techniques are combined. The present invention accomplishes this objective by first providing a data set of known elution times of known peptides. This data is typically taken from multiple separation experiments. It is then a further object of the present invention to create a plurality of vectors, each vector having a plurality of dimensions, and each dimension representing the amino acids present in each of these known peptides from the data set. As used herein, the term "vector" means an ordered collection of n dimensions; such that a vector having n attributes is an ordered collection of n dimensions. The elution time of any protein may then be predicted by first creating a vector by assigning dimensional values for the amino acids of at least one hypothetical peptide and then calculating a predicted elution time for the vector by performing a multivariate regression of the dimensional values of the hypothetical peptide using the dimensional values of the known peptides. Preferably, the multivariate regression is accomplished by the use of an artificial neural network (hereinafter referred to as an "ANN"), and more preferably, the ANN is a "feed forward" ANN. Training the ANN may be accomplished by any of the training methods known in the art, including, but not limited to gradient descent algorithms and conjugate gradient algorithms. Preferred gradient descent algorithms include, but are not limited to a backpropagation algorithm and a quickprop algorithm. Prior to the assignment of the vectors assigned to each of the known peptides in the data set and the dimensional values of the hypothetical peptide, it is preferable to normalize the elution times of the multiple separation experiments used to generate the data set using a linear or non-linear function. It is further preferred to optimize this Function by performing multiple regressions. The preferred method for the multiple regressions is a genetic algorithm.

The operation and use of the method of the present invention is described in a detailed description of a preferred embodiment of the present invention below. Those having skill in the art will readily recognize equivalent methods exist for the particular algorithms selected for the multivariate regression, the transfer function, and the method used to train the ANN in this preferred embodiment. Similarly, while the preferred embodiment describes the method of the present invention as it was applied in a liquid chromatograph coupled with a mass spectrometer, those having skill in the art will recognize that the method of the present invention is applicable with or without the use of the mass spectrometer, and the data provided by the mass spectrometer. Further, those having skill in the art will similarly recognize that the benefits provided by the present invention are also applicable if the mass spectrometer is replaced with other suitable detection means. It will also be apparent that while the preferred embodiment describes the method of the present invention in conjunction with liquid chromatography, the present invention should be understood to include both normal and reversed phase chromatography, and further may readily be utilized with other separation techniques, including without limitation, electrophoretic separations. Accordingly, it will be apparent to those skilled in the art that many changes and modifications may be made from the preferred embodiment described herein without departing from the invention in its broader aspects, and all separation methodologies, whether used with or without a detection means such as a mass spectrometer, and all equivalent algorithms for the multivariate regression, transfer functions, and methods used to train an ANN should be interpreted as falling within the true spirit and scope of the invention as set forth in the appended claims.

DETAILED DESCRIPTION OF A PREFERRED EMBODIMENT OF THE INVENTION

Figure 1:
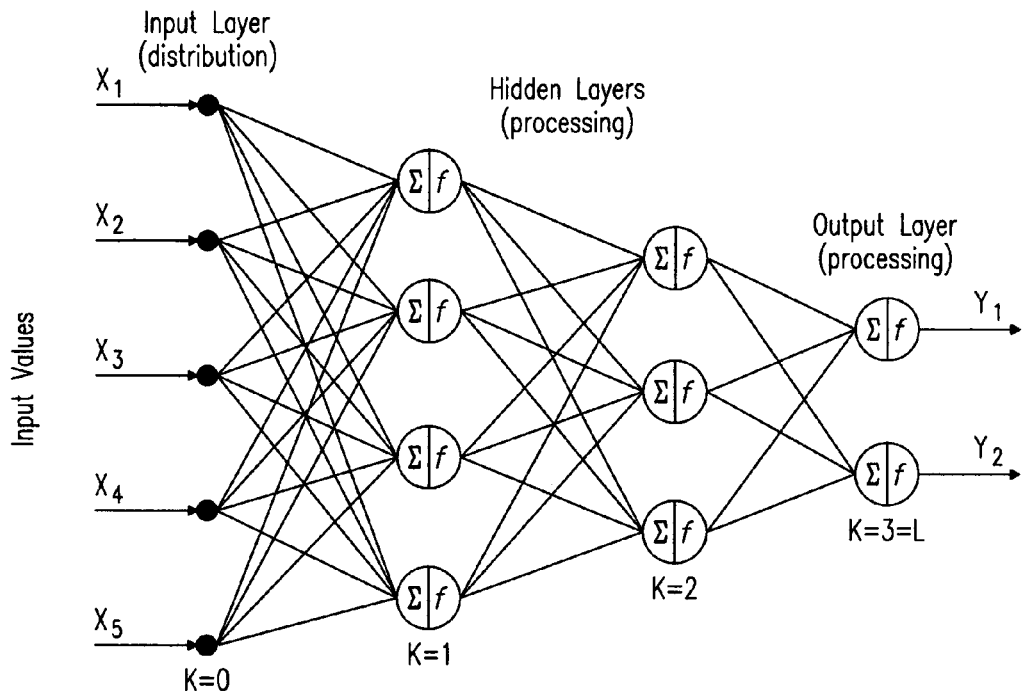
FIG. 1 is a schematic drawing of a typical three layer neural network showing the flow of signals from left to right.

A set of experiments was undertaken to demonstrate a preferred embodiment of the present invention. Briefly, an ANN was deployed for predicting the reversed-phase liquid chromatography retention times of peptides enzymatically digested from proteome-wide proteins. In order to enable the comparison of the numerous LC-MS data sets, a genetic algorithm (hereinafter "GA") was developed to normalize the peptide retention data into a range (from 0 to 1), improving the peptide elution time reproducibility to about 1%. The network developed in this study was based on amino acid residue composition and consists of 20 input, 2 hidden and 1 output nodes (20-2-1). A data set of about 7000 confidently identified peptides from the microorganism *Deinococcus radiodurans* was used for the training of the ANN. The ANN was then used to predict the elution times for another set of 5200 peptides tentatively identified by MS/MS from a different microorganism (*Shewanella oneidensis*). The model was found to predict the peptides of elution time with up to 54 amino acid residues (the longest peptide identified after tryptic hydrolysis of *S. oneidensis*) with an average accuracy of ~3%. This predictive capability was then used to distinguish with high confidence isobar peptides otherwise indistinguishable with Fourier transform ion cyclotron resonance mass spectrometry as well as to uncover peptide misidentifications. Thus, integration of ANN peptide elution time prediction in the proteomic research will increase both the number of protein identifications and their confidence.

*D. radiodurans* and *S. oneidensis* cells were cultured in TGY medium to an approximate 600 OD of 1.2 and harvested by centrifugation at 10,000 g at 4° C. Prior to lysis, cells were resuspended and washed three times with 100 mM ammonium bicarbonate and 5 mM EDTA (pH 8.4). Cells were lysed by beating with 0.1-mm acid zirconium beads for three 1-min cycles at 5000 rpm. The samples were incubated on ice for 5 min between each cycle of bead beating. The supernatant containing soluble cytosolic proteins was recovered after centrifugation at 15,000 g for 15 min to remove cell debris. Proteins were denatured and reduced by addition of guanidine hydrochloride (6 M) and DTT (1 mM), respectively, followed by boiling for 5 min. Prior to digestion, samples were desalted using a 5000 molecular weight cut-off "D-salt" gravity column (Pierce, Rockfor, Ill.) equilibrated in 100 mM ammonium bicarbonate (pH 8.4). Proteins were enzymatically digested at an enzyme/protein ration of 1:50 (w/w) using sequencing grade modified trypsin (Promega, Madison, Wis.) at 37° C. for 16 h.

HPLC-grade water and acetonitrile were purchased from Aldrich (Milwaukee, Wis.). Fused-silica capillary columns (30–60 cm, 150 µm i.d.×360 µm o.d., Polymicro Technologies, Phoenix, Ariz.) were then packed with 5-µm C18 particles as described in Shen, Y.; Zhao, R.; Belov, M. E.; Conrads, T. P.; Anderson, G. A.; Tang, K.; Pasa-Tolic L.; Veenstra, T. D.; Lipton, M. S.; Udseth, H. R.; Smith, R. D.; Anal. Chem. 2001, 73, 1766–1775, the entire contents of which are hereby incorporated herein by this reference. Briefly, capillary RPLC was performed using an ISCO LC system (model 100DM, ISCO, Lincoln, Neb.). The mobile phases for gradient elution were (A) acetic acid/TFA/water (0.2:0.05:100 v/v) and (B) TFA/acetonitrile/water (0.1:90:10, v/v). The mobile phases, delivered at 5000 psi using two ISCO pumps, were mixed in a stainless steel mixer (~2.8 mL) with a magnetic stirrer before flow splitting and entering the separation capillary. Fused-silica capillary flow splitters (30-mm i.d. with various lengths) were used to manipulate the gradient speed. Capillary RPLC was coupled on-line with MS through an ESI interface (a stainless steel union was used to connect an ESI emitter and the capillary separation column). The peptide database has been generated by using several mass spectrometers including 3.5, 7, and 11.4 telsa FTICR instruments (described in detail in Harkewicz, R.; Belov, M. E.; Anderson, G. A.; Paša-Tolić, L.; Masselon, C. D.; Prior, D. C.; Udseth, H. R.; Smith, R. D.; J. Am. Soc. Mass Spectrom. 2002, 13, 144–154, and references therein, the entire contents of which are hereby incorporated by this reference), as well as several ion-trap mass spectrometers (LCQ, LCQ Duo, LCQ DecaXP; ThermoFinnigan, San Jose, Calif.). The ANN software used was NeuroWindows version 4.5 (Ward Systems Group, USA) and utilized a standard backpropagation algorithm on a Pentium 1.5 GHz personal computer.

ANNs based approaches have advantages in comparison with classical statistical methods that include a capacity to self-learn and to model complex data without the need for detailed understanding of the underlying phenomena.

A feed-forward neural network model, sometimes called a backpropagation neural network due to its most common learning algorithm, was used for these experiments. It is composed of large number of neurons, nodes, or processing elements organised into a sequence of layers, as described in Werbos, P. J.; Beyond regression: New tools for predictive and analysis in the behavioural sciences, PhD Thesis, Harvard University, Cambridge, Mass., 1974, and Werbos, P. J.; The Roots of Backpropagation, John Wiley & Sons, New York, 1994, the entire contents of each of which are hereby incorporated herein by this reference. The architecture of these ANN models contain at least two layers: an input layer with one node for each variable in a data vector and, an output layer consisting of one node for each variable to be investigated. Additionally, one or more hidden layers can be added between the input and output layer if the complexity of the data so require. Nodes in any layer can be fully or partially connected to nodes of a succeeding layer as shown in FIG. 1, where each hidden or output node receives signals in parallel. The input signal to a node is modulated by a weight (w) along each link. The net input to a node is thus a function of all signals to a node and all of its associated weights. For example the net input for a node j is given by:

$$net_j = \sum_i w_{ji} O_i \qquad \text{(Eq-1)}$$

Where i represents nodes in the previous layer, $w_{ji}$ is the weight associated with the connection from node i to node j, and $O_i$ is the output of node i.

The final output signal of a node is usually confined to a specified interval, say between zero and one. The net input to the neuron thus underwent an additional transformation using a transfer function. There are several transfer functions available, satisfying a requirement of continuity, set by the backpropagation algorithm. The most popular one is the sigmoid function given by:

$$O_j = \frac{1}{(1 + e^{-net_j})} \qquad \text{(Eq-2)}$$

In essence, these equations applied to nodes in the hidden and output layers allows these ANNs to perform multiple multivariate non-linear regression using sigmoidal functions, and because of the parallel processing of nodes within each layer, these ANNs have the ability to learn multivariate non-linear functions.

The process of adapting the weights to an optimum set of values is called training the neural network. In order to train the neural network there exist several training algorithms. Examples of such functions are detailed in Rumelhart, D. E.; Hinton, G. E.; Williams, R. J.; Learning internal representations by error propagation, Parallel Distrubuted Processing: Explorations in the Microstructures of Cognition. Vol. 1: Foundations, Rumelhart, D. E.; McClelland, J. L.; (eds.), MIT Press, Cambridge, Mass., USA, pp. 318–362, 1986, the entire contents of which are hereby incorporated herein by this reference. The backpropagation algorithm selected for these experiments is one example, however, the present invention should in no way be viewed as limited to this example.

An "intelligent" algorithm for the normalization of retention time was desired to compare a large number of LC-MS experiments, due to the variability associated with constant high-pressure capillary LC separations using syringe pumps. Small changes in split ratio, column lengths, column packings, void volumes etc. have been known to lead to some retention time variability. Thus, all peptide retention times were normalized to the range [0, 1] by using a genetic algorithm (GA).

As described in Holland, J. H.; Adaptation in Natural and Artificial Systems. University of Michigan Press, Ann Arbor, Mich., 1975, and Goldberg, D. E.; Genetic Algorithms in Search, Optimisation and Machine Learning. Addison-Wesley, Reading, Miss., 1989, (the entire contents of each of which are hereby incorporated herein by this reference), a GA is an algorithm based on evolutionary computation and survival of the fittest, and is often applied to optimization problems such as optimizing the free variables in a hypothesis function. Solutions to problems are coded as individuals, which evolve through generations. An individual in our coding is a vector of real values (line functions) of slopes and intercepts for each experiment being normalized. The fittest individuals in each generation breed the next generation through crossover and mutation operators, recombining best "genes." The "genes" in the offsprings are then perturbed in the next step by a small value and by a small probability. This iterative process causes the best solution, the fittest individuals, to be incrementally refined.

Figure 2:
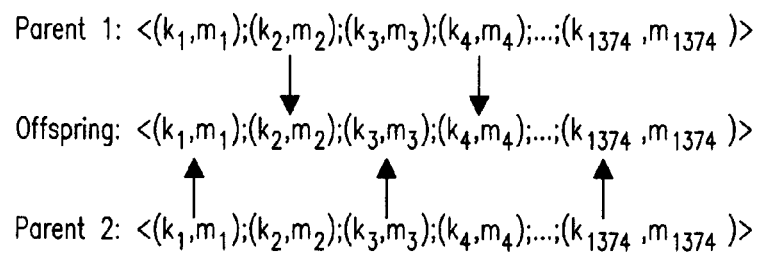
FIG. 2 is a schematic drawing showing the recombination of two parent's genes into a new offspring in a genetic algorithm.

The GA was applied to 51,150 (9,121 different) peptides identified from 687 LC-MS-MS analyses to establish a common timeline so that the same peptides eluted at the same normalized elution time (NET) in the different separations. The GA was set up to optimise the two linear equation variables, k and m in y=kx+m, for each experiment (FIG. 2 shows coding of the individuals): one variable (m) normalized the start of the recording time and the other (k) normalized the gradient speed. The GA optimised these two variables for each separation to reduce the variance function of specific peptides, i.e. the regressed elution times for each separation. This optimization scheme of multiple linear regressions normalized the peptide elution times into a common [0,1] range.

The average variance of NETs for the peptides (5270) detected in more than one experiment is 0.000276 (standard deviation 0.016615). Preferably, while not meant to be limiting, a set of standard peptides is selected which elute at the beginning, the middle and the end of the chromatogram to further improve the normalization of retention times.

The ANN training set consisted of 6958 confidently identified D. radiodurans peptides measured by the RPLC/ESI-ion-trap MS, and further verified with high mass measurement accuracy using RPLC-ESI-FTICR-MS to exist in the D. radiodurans polypeptide mixture. Each peptide was coded as a 20-dimensional vector consisting of the normalized number of each of the 20 amino acid residues making up the peptides. Each residue count was normalized to a fraction of the maximum count of that residue in any peptide in the D. radiodurans database. These peptide code vectors were repeatedly input into the ANN by the back-propagation algorithm to reduce output error. The output error is the squared difference between a target value of the ANN and the predicted value. In this case the target values were the known NETs of the peptides. The ANN thus learned the relationship between the coded peptide vectors and their measured NETs.

Figure 3:
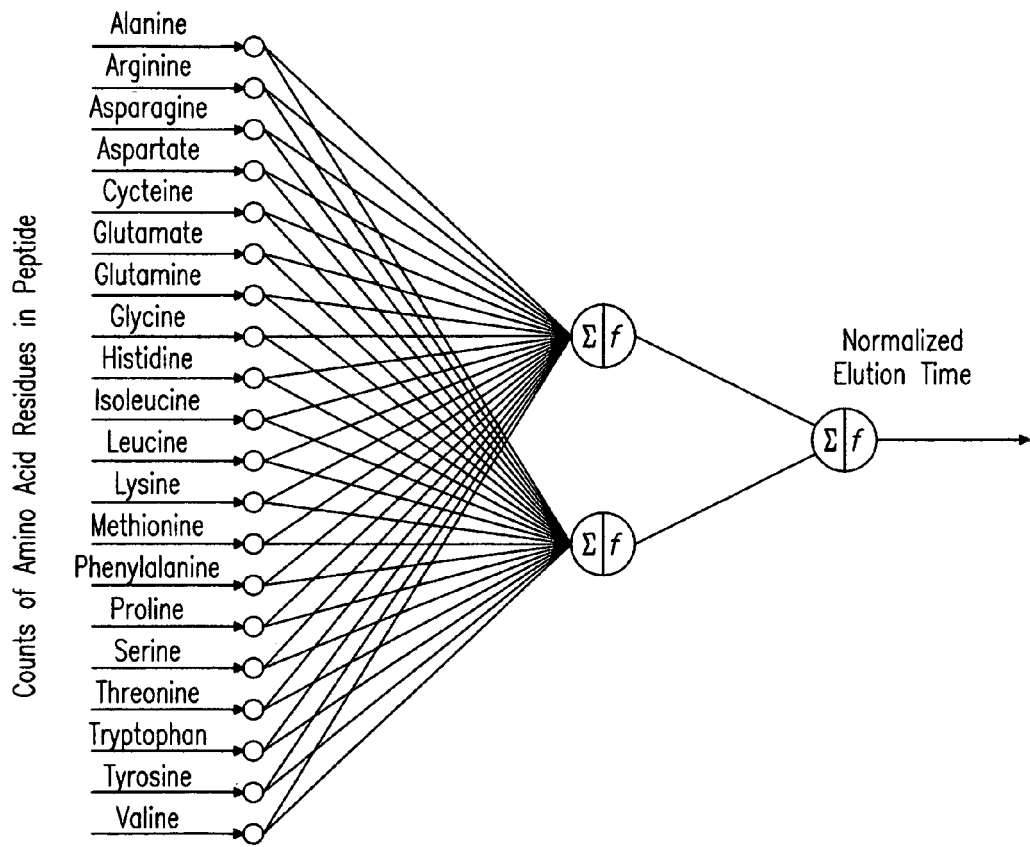
FIG. 3 is a schematic drawing showing the 20-2-1 neural network architecture used in a preferred embodiment of the present invention.

The hidden layer(s) configuration for the ANN was empirically determined by using a cross-validation data set during training. In general, a hidden layer with too few nodes may not sufficiently model the data. A hidden layer with too many nodes may overfit the data in the training set and not provide an effective predictive capability for new data. The ANN was trained with 97% of the DR peptides and cross-validated with the remaining data. Typically the cross-validation data sets are used to stop the training when the error for the data set ceases to decrease. Going beyond this point suggests that the ANN "learns" from noise in the training set that is not present in the cross-validation set. The experience in training ANNs with peptide elution data showed that the ANN could not be over-trained. Both the errors on the training and the cross-validation data sets rapidly converged to minimum values. A small improvement was realized by using 2 node hidden layer instead of no hidden layers. Increasing to three hidden nodes made an even smaller improvement. Table 1 shows error rates as a function of the number of hidden layer nodes in seven training sessions. The hidden layer could be increased to a large number of nodes without the back-propagation algorithm being able to reduce the errors or being able to overfit the data. A hidden layer with two nodes was used since it reduced the error to a near optimal level without potentially sacrificing generality. The training was stopped at 1000 epochs, as the errors appeared to have converged at different learning rates ranging from 0.001 to 0.1. The final ANN model with 20 input—2 hidden—and one output nodes (20-2-1) is depicted in FIG. 3.

Table 2 summarizes the calculated ANN weights of amino acid residues after training with the D. radiodurans peptides. From the weights we see that leucine is the amino acid that most affects peptide retention times.

Figure 4A:
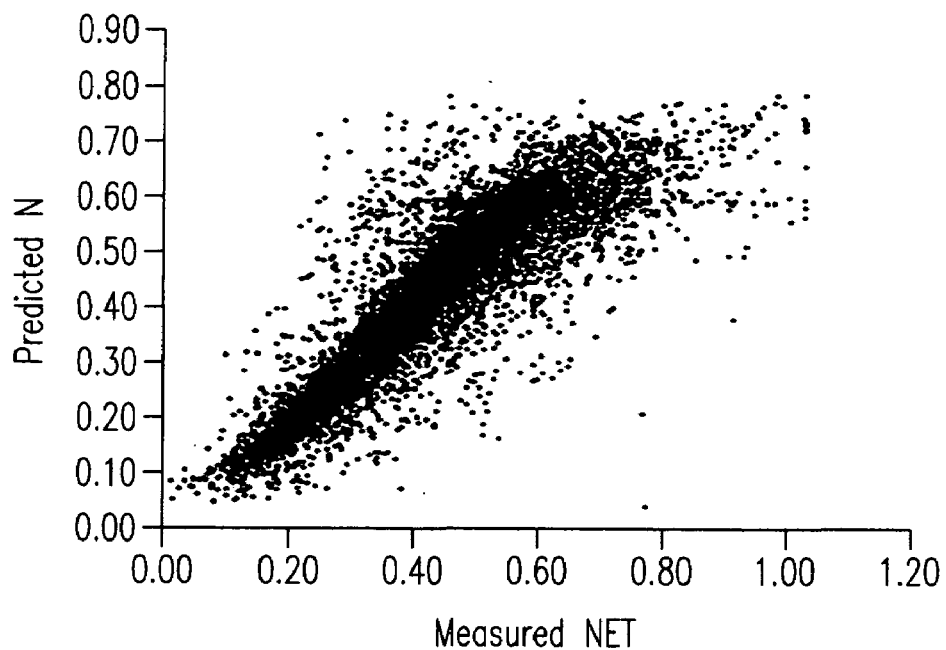
FIG. 4 is a graph showing measured vs. predicted normalised elution times among 42378 S. oneidensis peptides from 157 experiments which have been identified (a) 3 times (7080 peptides ), (b) 20 times (1270 peptides), (c) 40 times (536 peptides), (d) 60 times (259 peptides).

The ANN model was evaluated using peptides identified from the microorganism S. oneidensis, using RPLC-ESI-ion trap MS/MS. The average error for predicting S. oneidensis NETs for 7080 peptides from 157 analyses was 0.047983 or ~4.8%. FIG. 4a shows a plot of the predicted Nets for 7080 S. oneidensis peptides identified in 157 different separations. These results should be considered worst case because of the uncertainly in peptide identifications—S. oneidensis peptides, unlike the D. radiodurans peptides in the training set, were not validated using accurate mass measurements—. Furthermore the data in FIG. 4a, suggests the extremes in errors for LC elution predictions but does not clearly show the distribution of errors around the mean. The plot also includes errors due to variations between separations, which are not fully eliminated in the normalization process (and would benefit from the use of elution time calibrants).

Figure 4B:
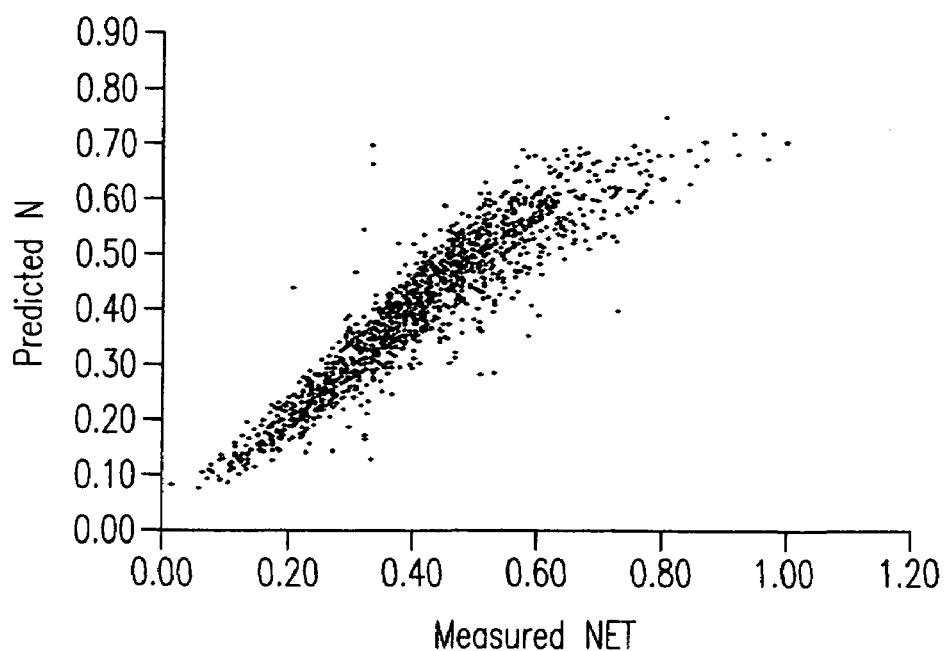
Figure 4C:
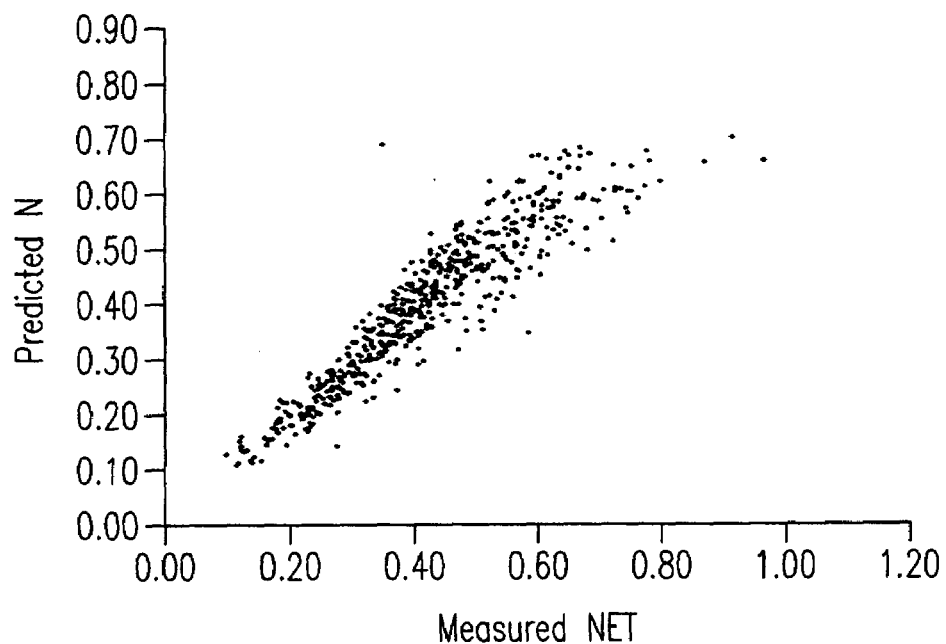
Figure 4D:
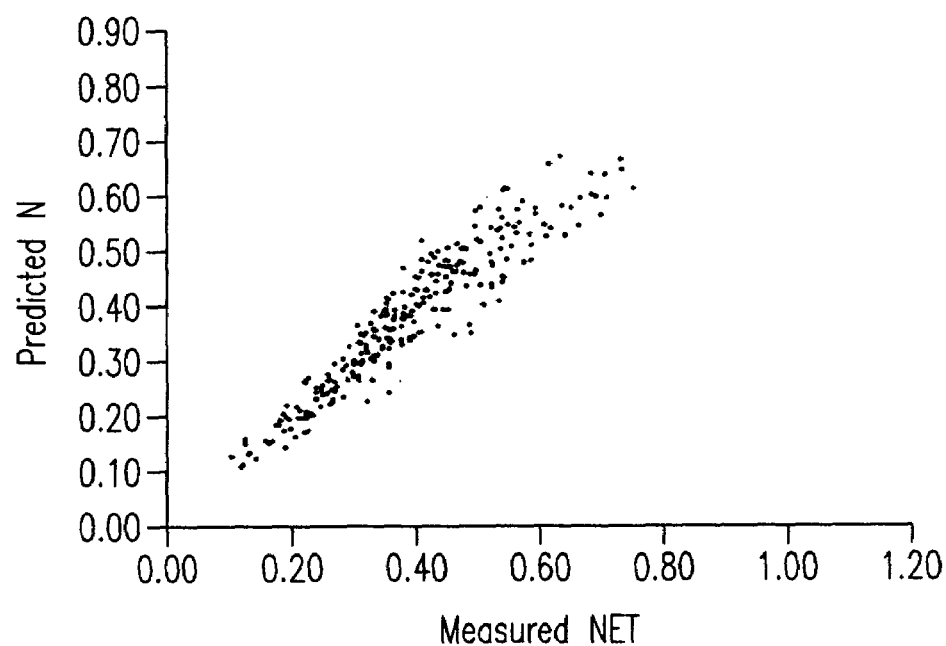

A significant number of S. oneidensis peptides were identified one or only a few times across all 157 experiments, suggesting that they may be miss-identifications. This is supported by the observation that the average prediction error decreases rapidly when the model is tested with peptides required to occur in increasing number of experiments. A more rigorous error measurement from S. oneidensis peptides from the same number of experiments, and each peptide occurring at least 20, 40 or 60 times to reduce spurious misidentifications, yielded an average error of 3.86, 3.67 and 3.66% respectively (see FIG. 4b-d). It can be seen that the peptides with poor correlation with these experiments (i.e. highly dispersed in the plots) are eliminated when only the peptides occurred at least 60 times were selected, again suggesting that infrequently seen peptides are possibly misidentified. Furthermore, preliminary LC-FTICR experiments of the S. oneidensis implied that multiple ion-trap identifications are probably correct based on accurate mass measurements. Thus, as the probability of correct identifications is increased, a better correspondence with predicted elution times is observed.

Figure 5:
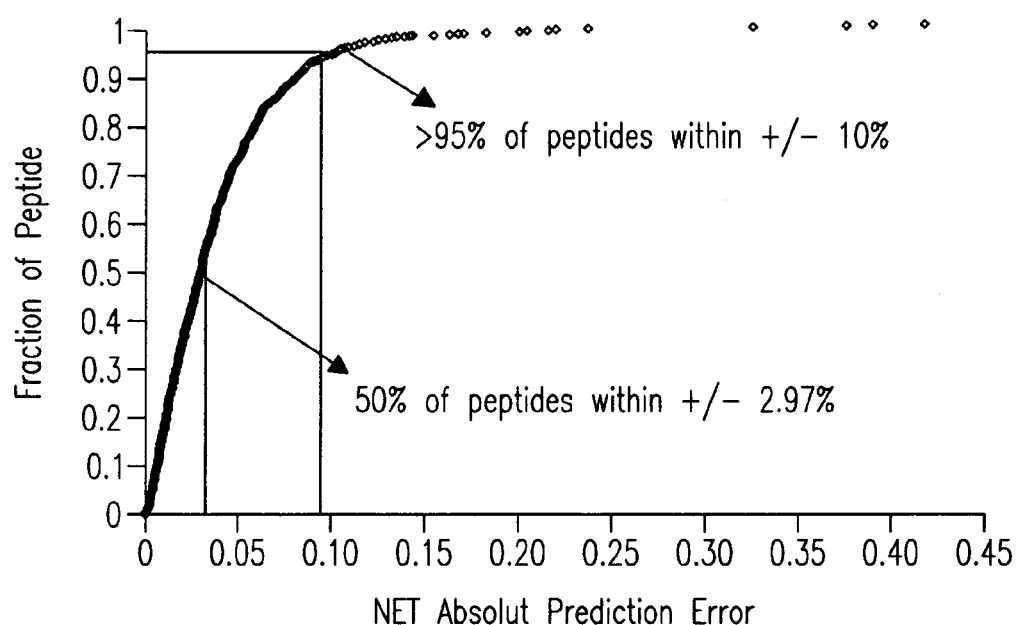
FIG. 5 is a graph showing the prediction error distribution for 1270 *S. oneidensis* peptides that were tentatively identified at least 20 times using the program SEQUEST. The graph shows the fraction of peptides vs. the NET error levels. For example, the graph shows that 50% of the peptides have less than a 3% prediction error, and more than 95% have less than 10% error.

FIG. 5 shows the error distribution of these 1270 S. oneidensis peptides which have been identified at least 20 times. This curve is assumed to approach the true distribution of the prediction model's performance for correctly identified peptides. For this peptide set, 50% are predicted within +/−2.97% of the measured NETs, and more than 95% are predicted within +/−10% of the measured NETs.

One of the major advantages of our model in relation to previous ones is that it provides more accurate prediction for longer peptides. As it can been seen from Table 3, the average error is very low for peptides up to 20-mer size, the error then increases just slightly for longer peptides.

Figure 6:
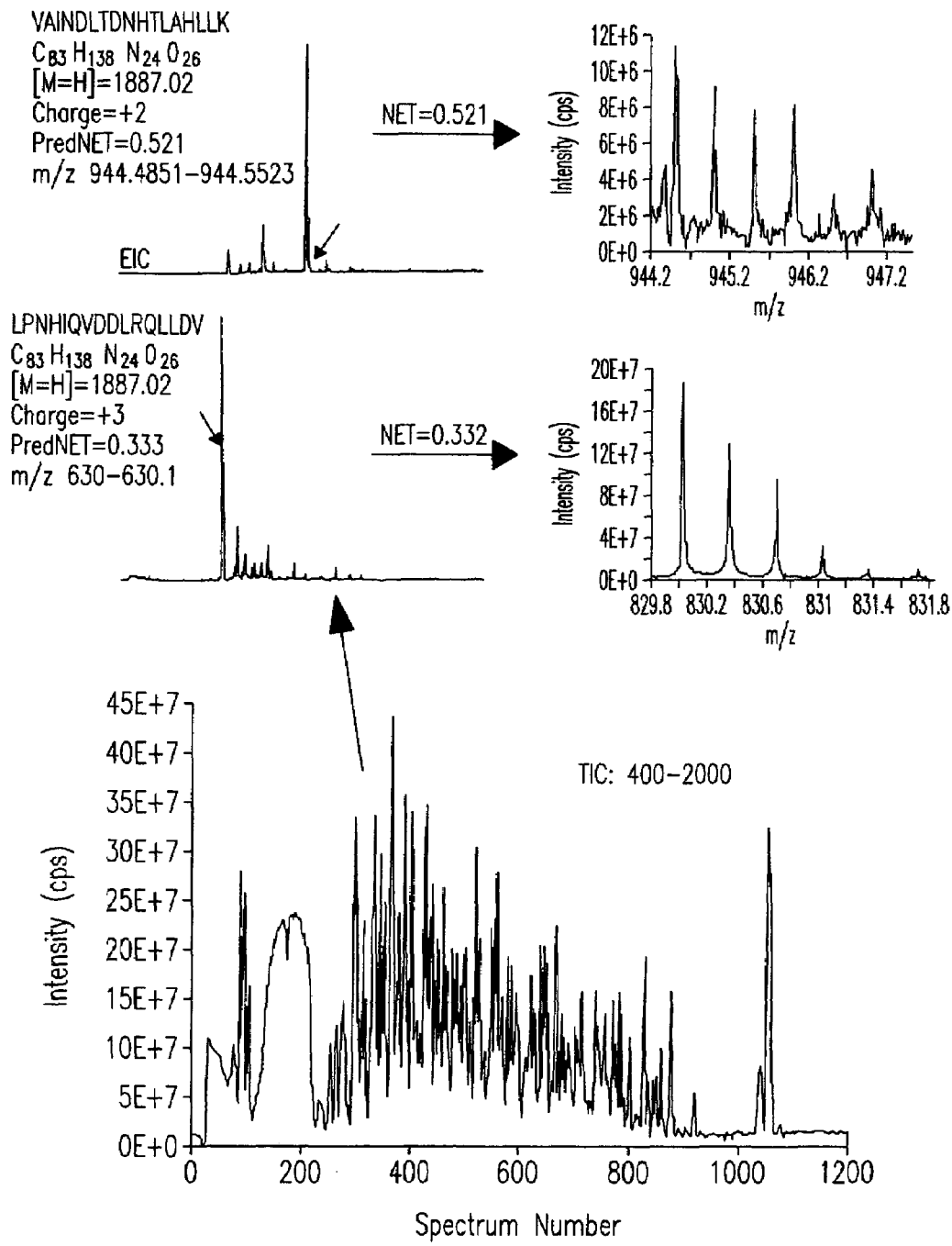
FIG. 6 is a schematic of an example of the more confident identification of two isobaric peptides by using peptide predicted elution times as an additional metric. The isobaric peptides LPNHIQVDDLRQLLDV (SEQ ID No. 1) and VAINDTDNHTLAHLLK (SEQ ID No. 2) have a different normalised elution time (NET), which has allowed their differentiation. The figure shows the total ion current (TIC), the corresponding extracted ion currents (EIC) and the mass spectra of these peptides.

The very fact that not all peptides can be correctly identified by either accurate mass measurement or MS/MS experiments has prompted this research into utilizing elution time as an additional metric for identifying peptides. The use of peptide elution prediction will be particularly interesting for the identification of isobaric peptides by LC-FTICR. As it can be seen from FIG. 6 it was possible to distinguish between the isobaric D. radiodurans peptides LPNHIQVD-DLRQLLDV (SEQ ID No. 1) and VAINDTDNHT-LAHLLK (SEQ ID No. 2) due to their significantly different elution times, accurately predicted with our model. While these two peptides have the same molecular formula, interestingly they have different charges. Furthermore, as shown from Table 4, several isobaric peptides (undistinguishable even with 1 ppm mass accuracy) have different retention times and were identified with our model. Moreover, it is also possible to distinguish isomeric peptides, which have different Ile/Leu ratios (i.e. IVIEIK (SEQ ID No.3) and VILLEK (SEQ ID No. 4)) due to the different ANN weights assigned to these amino acid residues. Some of the peptides of course will have very similar retention times (i.e. the isobar peptides ANAAINSGAFK (SEQ ID No. 8) and IIAAGANVVR (SEQ ID No. 9) have the same NET=0.26, data not shown). This approach will be even more useful for proteomes of higher complexity, where the number of possible peptides is greatly increased. For example, in a typical 7 ppm "window" between 1605.851 and 1605.863 Da, the human proteome codes for 12 tryptic peptides. But, three peptides (QTFEAAILTQLHPR (SEQ ID No. 5), TLH-SLTQWNGLINK (SEQ ID No. 6) and LLFLVGTASNP-HEAR (SEQ ID No. 7)) have masses of 1605.86264 Da and are indistinguishable by mass. Importantly, however, these peptides are predicted to have much different predicted LC retention times.

It must be pointed out that the preferred embodiment described herein only takes into account the peptides amino acid composition and not their sequence, thus isomeric peptides (same amino acids in a different order) are predicted to elute at the same time, although it has been shown that such peptides are often separated in LC. Sequence-dependent effects such as conformational and nearest-neighbor effects may be additional factors for deviations from predicted retention times. Recently, Wimley et al. (52) have shown that occlusion effects may occur in the case of guest (X) side chains in the host-guest pentapeptides ACWL-X-LL that may lead in changes in the overall hydrophobicity of the peptide. The present invention should be understood to encompass more sophisticated ANNs than those described in these experiments, which would incorporate selected sequence features, thereby enhancing the predictions, including the ability to distinguish sequence variations. These ANNs would utilize larger experimental datasets relative to different peptide retention times described herein, which would further include some aspects of sequence information in the ANN. Finally the experiments described herein have an inherent weakness relative to the use of tryptic peptides for its training. Thus, the peptides used in this study include Arg and Lys only once, except when miscleavages occur. Due to their basic character these amino acids change the pKa/apparent charge of these peptides, and consequently their retention times. As a result the values given for Arg and Lys might not apply for non-tryptic peptides having additional Arg or Lys residues in their structure. While this should not be a problem in the case of ideal trypsin proteolysis, such miscleavages are commonly observed in global proteomic studies. To overcome this problem, the ANN should be trained to more correctly predict retention times for peptides containing more than one Lys or Arg residue.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

The invention claimed is:

1. A method for predicting the elution time of peptides in liquid separations comprising the steps of:
   a. providing a data set of known elution times of known peptides,
   b. creating a plurality of vectors, each vector having twenty dimensions, each dimension representing an amino acid potentially present in each of said known peptides, and each vector associated with the elution time of said peptide,
   c. creating a hypothetical vector by assigning dimensional values for at least one hypothetical peptide, and
   d. calculating a predicted elution time for said hypothetical vector by performing at least one multivariate regression fitting said hypothetical peptide to said plurality of vectors.

2. The method of claim 1 comprising the further step of normalizing the known elution times prior to creating said plurality of vectors.

3. The method of claim 1 wherein the multivariate regression is performed using an artificial neural network.

4. The method of claim 3 wherein the artificial neural network trained with a method selected from the group consisting of gradient descent algorithms and conjugate gradient algorithms.

5. The method of claim 4 wherein the artificial neural network trained with a gradient descent algorithm selected from the group consisting of a backpropagation algorithm and a quickprop algorithm.

6. The method of claim 2 wherein normalization is performed by optimizing a function using multiple regressions.

7. The method of claim 6 wherein the multiple regressions are calculated using a genetic algorithm.

8. The method of claim 6 wherein the function is selected from the group consisting of linear and non-linear functions.

9. The method of claim 1 wherein the liquid separation is performed by a method selected from the group consisting of liquid chromatography, both standard and reverse phase, electrophoretic separations, capillary electrophoresis; field flow fractionation, and combinations thereof.

* * * * *

UNITED STATES PATENT AND TRADEMARK OFFICE
CERTIFICATE OF CORRECTION

PATENT NO. : 7,136,759 B2  Page 1 of 1
APPLICATION NO. : 10/323387
DATED : November 14, 2006
INVENTOR(S) : Lars J. Kangas et al.

It is certified that error appears in the above-identified patent and that said Letters Patent is hereby corrected as shown below:

Please correct paragraph 0001 of the application and Column 1, lines 8 through 11 of the issued patent as follows:

The invention was made with Government support under grant number RR018522 from the U.S. National Institutes of Health and contract DE-AC05-76RL01830 awarded by the US Department of Energy. The government has certain rights in the invention.

Signed and Sealed this
Eleventh Day of September, 2012

David J. Kappos
*Director of the United States Patent and Trademark Office*